United States Patent
Thompson et al.

(10) Patent No.: US 9,255,091 B2
(45) Date of Patent: Feb. 9, 2016

(54) BENZOTHIAZOLE-BASED PYRIDINIUM COMPOUNDS

(75) Inventors: Charles M. Thompson, Missoula, MT (US); Sandip Bharate, Pune (IN)

(73) Assignee: The University of Montana, Missoula, MT (US)

( * ) Notice: Subject to any disclaimer, the term of this patent is extended or adjusted under 35 U.S.C. 154(b) by 801 days.

(21) Appl. No.: 13/592,386

(22) Filed: Aug. 23, 2012

(65) Prior Publication Data

US 2015/0259336 A1 Sep. 17, 2015

Related U.S. Application Data

(60) Provisional application No. 61/526,596, filed on Aug. 23, 2011.

(51) Int. Cl.
*A61K 31/44* (2006.01)
*C07D 213/72* (2006.01)
*C07D 417/12* (2006.01)

(52) U.S. Cl.
CPC .................................. *C07D 417/12* (2013.01)

(58) Field of Classification Search
None
See application file for complete search history.

(56) References Cited

U.S. PATENT DOCUMENTS

2006/0079533 A1  4/2006 Nieman et al.

OTHER PUBLICATIONS

Silva, T. Mini Rev Med Chem 2005 vol. 5 pp. 893-914.*
Vassar, R. Alzheimers Res Ther 2014 6-89 pp. 1-14.*
Bharate and Thompson, "Antimicrobial, Antimalarial, and Antileishmanial Activities of Mono- and Bis-quaternary Pyridinium Compounds," *Chem. Biol. Drug Des.* 76:546-551 (2010).
Bharate et al., "Bisquaternary Pyridinium Oximes: Comparison of in Vitro Reactivation Potency of Compounds Bearing Aliphatic Linkers and Heteroaromatic Linkers for Paraoxon-inhibited Electric Eel and Recombinant Human Acetylcholinesterase," *Bioorg. Med. Chem.* 18:787-794 (2010).
Bharate et al., "New Series of Monoquaternary Pyridinium Oximes: Synthesis and Reactivation Potency for Paraoxon-Inhibited Electric Eel and Recombinant Human Acetylcholinesterase," *Bioorg. Med. Chem Let.* 19:51010-5104 (2009).
Bharate et al., "Thionate versus Oxon: Comparison of Stability, Uptake, and Cell Toxicity of (14CH3O)2-Labeled Methyl Parathion and Methyl Paraoxon with SH-SY5Y Cells," *J. Agric. Food Chem.* 58:8460-8466 (2010).
Bourne et al., "Freeze-frame Inhibitor Captures Acetylcholinesterase in a Unique Conformation," *Proc. Nat. Acad. Sci.* 101(6): 1449-1454 (2004).
Camps et al., "Novel Donepezil-based Inhibitors of Acetyl- and Butyrylcholinesterase and Acetylcholinesterase-induced β-Amyloid Aggregation," *J. Med. Chem.* 51(12):3588-3598 (2008).
De Ferrari et al., "Thioflavin T is a Fluorescent Probe of the Acetylcholinesterase Peripheral Site that Reveals Conformational Interactions between the Peripheral and Acylation Sites," *J. Biol. Chem.* 276: 23282-23287 (2001).
Doorn et al., "Identification of Butyrlcholinesterase Adducts after Inhibition with Isomalathion Using Mass Spectrometry: Difference in Mechanism between (1R)- and (1S)-Stereoisomers," *Toxicol Applied Pharmacol.* 176:73-80 (2001).
Doorn et al., "Inhibition of Acetylcholinesterase by (1S,3S)-Isomalathion Proceeds with Loss of Thiomethyl: Kinetic and Mass Spectral Evidence for an Unexpected Primary Leaving Group," *Chem. Res. Toxicol.* 13:1313-1320 (2000).
Etoga et al., "Conformationally-restricted Amino Acid Analogues Bearing a Distal Sulfonic Acid Show Selective Inhibition of System $X_C$ over the Vesicular Glutamate Transporter," *Bioorg. Med. Chem. Let.* 20:2680-2683 (2010).
Guo et al., "Inhibition of acetylcholinesterase by chromophore-linked fluorophosphonates," *Bioorg. Med. Chem. Let.* 20:1194-1197 (2010).
Huh and Thompson, "Enantioenriched N-(2-Chloroalkyl)-3-acetoxypiperidines as Potential Cholinotoxic Agents. Synthesis and Preliminary Evidence for Spirocyclic Aziridinium Formation," *Tetrahedron* 51(21):5935-5950 (1995).
Hyatt et al., "Inhibition of Acetylcholinesterase by the Anticancer Prodrug CPT-11," *Chemico-Biological Interact.* 157-158:247-252 (2005).
Johnson et al., "Unmasking Tandem Site Interaction in Human Acetylcholinesterase. Substrate Activation with a Cationic Acetanilide Substrate," *Biochem.* 42(18):5438-5452 (2003).
Ryu et al., "Comparative Anticholinesterase Potency of Chiral Isoparathion Methyl," *Chem. Res. Toxicol.* 4:517-520 (1991).
Thompson et al., "Preparation, Analysis, and Anticholinesterase Properties of O,O-Dimethyl Phosphorothioate Isomerides," *Chem. Res. Toxicol.* 2:386-391 (1989).

* cited by examiner

*Primary Examiner* — Heidi Reese
(74) *Attorney, Agent, or Firm* — Minerva, PLLC; Zachary Scott

(57) ABSTRACT

The compositions of the invention are novel benzothiazol-based pyridinium compounds with potent acetylcholinesterase (AChE) and butyrylcholinesterase (BChE) inhibitory activities. Such compositions can be used, for example, to treat Alzheimer's Disease and other neurodegenerative disorders. The compounds of the invention can also be used to prevent or treat the neurotoxic effects of nerve agents (e.g., sarin gas or insecticides).

11 Claims, 4 Drawing Sheets

IC$_{50}$ values of most active inhibitors of EeAChE, rHuAChE and HuBChE.

R" = H

| | R' | R | IC$_{50}$ ± SEM (nM) | | | Selectivity for AChE | |
|---|---|---|---|---|---|---|---|
| | | | EeAChE | rHuAChE | HuBChE | IC$_{50}$(BChE) / IC$_{50}$ (EeAChE) | IC$_{50}$(BChE) / IC$_{50}$ (rHuAChE) |
| 4a | OCH$_3$ | H | 441 ± 75 | 186 ± 5 | 3013 ± 465 | 7 | 16 |
| 4b | OCH$_3$ | 4-F | 542 ± 140 | 223 ± 5 | 5628 ± 253 | 10 | 25 |
| 4c | OCH$_3$ | 2,6-di-F | 408 ± 91 | 203 ± 20 | 826 ± 49 | 2 | 4 |
| 4d | F | 4-F | 500 ± 45 | 269 ± 22 | 8164 ± 567 | 16 | 30 |
| 4e | NO$_2$ | 4-F | 25 ± 1 | 96 ± 9 | 11886 ± 1002 | 475 | 124 |
| Donepezil | | | 26[10] | 15[10] | 7273[11] | 280 | 485 |

BENZOTHIAZOLE-BASED PYRIDINIUM COMPOUNDS

CROSS-REFERENCE TO RELATED APPLICATIONS

This application claims the benefit of the filing date of U.S. Provisional Patent Application Ser. No. 61/526,596, filed Aug. 23, 2011, the disclosure of which is incorporated by reference in its entirety.

STATEMENT REGARDING FEDERALLY SPONSORED RESEARCH OR DEVELOPMENT

This invention was made in part with government support under Grant Nos. UO1-ES016102 and P30-NS055022 awarded by the National Institutes of Health. The government has certain rights in the invention.

BACKGROUND OF THE INVENTION

Alzheimer's disease (AD) is an irreversible, progressive neurodegenerative disorder, which occurs gradually, resulting in memory loss, behavior disturbances, personality changes and a decline in cognitive abilities; it is also the most common cause of dementia among the elderly. Neuropathological studies have demonstrated that cholinergic functions in the basal forebrain and cortex decline due to senile dementia during AD. While there are no successful treatments currently available to stop its degenerative progress, a promising therapeutic strategy for activating the cholinergic functions has been the use of cholinomimetic agents such as donepezil, galantamine, rivastigmine, tacrine, and memantine, each approved for human use by the FDA. With the exception of memantine, all are potent, reversible inhibitors of acetylcholinesterase (AChE; EC 3.1.1.7). Use of these drugs is limited in utility, however, due to adverse side-effects, such as hepatotoxicity, gastrointestinal disturbance, and problems with bioavailability. For this reason, research efforts aimed at improving the pharmacological profile of the prototypes continue.

AChE contains a narrow and deep active site gorge with two sites of ligand binding—an acylation site (or A-site) at the base of the gorge and a peripheral site (or P-site) near the gorge entrance. The P-site contributes to the catalytic efficiency of the enzyme by transiently binding substrates on their way to the acylation site, where a short-lived acyl enzyme intermediate is produced (Johnson et al., *Biochem.* 42:5438-5452 (2003)). The P-site, spanned by residues W286 (hAChE) near the mouth of the gorge and D74 (hAChE) near a constriction at the boundary between the P-site and the A-site, specifically binds fluorescent probe Thioflavin T (De Ferrari et al., *J. Biol. Chem.* 276: 23282-23287 (2001)). Thioflavin T, a benzothiazole-based fluorophore widely used to detect amyloid structure in proteins, binds selectively to the AChE P-site with an equilibrium dissociation constant of 1.0 μM. Donepezil (donepezil hydrochloride, trade name: Aricept®, E2020, CAS #120014-06-4, 2-(1-benzyl-piperidin-4-ylmethyl)-5,6-dimethoxy-indan-1-one), is an acetylcholinesterase inhibitor with $IC_{50}$ of 15 nM (hAChE), 26 nM (EeAChE) and 7273 nM (BuChE) (Hyatt et al., *Chem. Biol. Interact.* 157-158:247-252 (2005); and Camps et al., *J. Med. Chem.* 51:3588-3598 (2008)). Thioflavin T appears to be a dual-site binding AChE inhibitor interacting with both A- and P-sites of AChE. New compound types capable of binding A- and P-sites incorporating thiazole heterocycles as a motif could improve selectivity toward AChE and thereby improve therapeutic utility against neurodegenerative diseases and disorders.

The primary molecular target of organophospate nerve agents, whether weaponized or used as insecticides, is AChE. As nerve agents may inhibit other enzymes and because the receptors for acetylcholine (muscarinic and nicotinic acetylcholine receptors) are widely expressed, these agents can impact a number of biological processes. In addition to well-known CNS effects, vascular and inflammatory effects of nerve agents include vasoconstriction, an increase in blood brain barrier permeability, as well as modulation of lymphocyte proliferation and cytokine production. Exposure to organophosphates used in weapons or insecticides can result in significant morbidity or death. Present treatment of organophosphate poisoning consists of post-exposure intravenous or intramuscular administration of various combinations of drugs, including carbamates (e.g., pyridostigmine), anti-muscarinics (e.g., atropine), and ChE-reactivators such pralidoxime chloride (2-PAM). Novel inhibitors of AChE that block the binding of organophosphates can be used as prophylactic treatments for patients (e.g., a human, such as soldier or farmer) at risk for exposure to an organophosphate insecticide or chemical agent.

All patents, patent applications, provisional patent applications and publications referred to or cited herein are incorporated by reference in their entirety to the extent they are not inconsistent with the teachings of the specification.

SUMMARY OF THE INVENTION

In one aspect of the invention, benzothiazole-based pyridinium compounds are presented and defined by the structural formula:

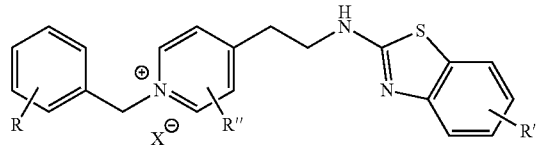

or a salt, ester or prodrug thereof, wherein the phenyl ring may contain one or more R substituent groups, the benzothiazole ring may contain one or more R' substituent groups, and the pyridine ring may contain one or more R" substituent groups; and wherein R is selected from the group consisting of hydrogen, a halogen, alkyl, cycloalkyl, aryl, heteroaryl, a 3' hydroxyl, a 5' hydroxyl, acyl, alkoxy, carboxy ester, carboxythiol ester, and an amide, any carbon atom of which may be optionally substituted;

R' is selected from the group consisting of hydrogen, a halogen, alkyl, cycloalkyl, aryl, heteroaryl, a 3' hydroxyl, a 5' hydroxyl, acyl, alkoxy, carboxyester, carboxythiol ester, and an amide, any carbon atom of which may be optionally substituted;

R" is selected from the group consisting of hydrogen, a halogen, alkyl, cycloalkyl, aryl, heteroaryl, a 3' hydroxyl, a 5' hydroxyl, acyl, alkoxy, carboxyester, carboxythiol ester, and an amide, any carbon atom of which may be optionally substituted; and X is selected from the group consisting of an organic or inorganic negatively-charged ion.

In one embodiment, the compound is selected from the following formulae:

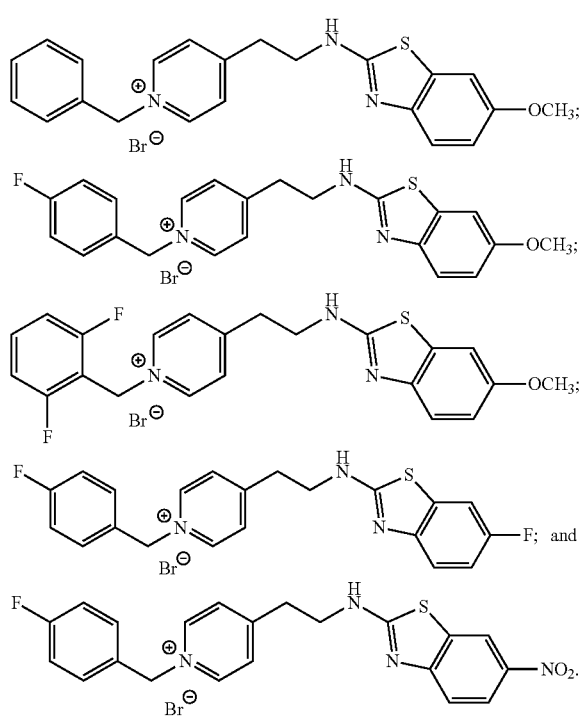

In another embodiment, the compound includes a pharmaceutically acceptable excipient.

In a second aspect of the invention, a method is presented for treating or preventing the development of a neurodegenerative disease by identifying a patient suffering from or at risk of developing a neurodegenerative disease and administering to the patient a therapeutically-effective amount of a compound represented by the following formula:

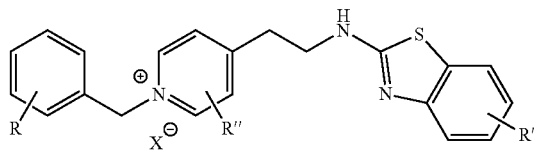

or a salt, ester or prodrug thereof, wherein the phenyl ring may contain one or more R substituent groups, the benzothiazole ring may contain one or more R' substituent groups, and the pyridine ring may contain one or more R" substituent groups; and wherein R is selected from the group consisting of hydrogen, a halogen, alkyl, cycloalkyl, aryl, heteroaryl, a 3' hydroxyl, a 5' hydroxyl, acyl, alkoxy, carboxyester, carboxythiolester, and an amide, any carbon atom of which may be optionally substituted;

R' is selected from the group consisting of hydrogen, a halogen, alkyl, cycloalkyl, aryl, heteroaryl, a 3' hydroxyl, a 5' hydroxyl, acyl, alkoxy, carboxyester, carboxythiolester, and an amide, any carbon atom of which may be optionally substituted;

R" is selected from the group consisting of hydrogen, a halogen, alkyl, cycloalkyl, aryl, heteroaryl, a 3' hydroxyl, a 5' hydroxyl, acyl, alkoxy, carboxyester, carboxythiolester, and an amide, any carbon atom of which may be optionally substituted; and X is selected from the group consisting of an organic or inorganic negatively-charged ion.

In one embodiment, the patient is a human. In another embodiment, the neurodegenerative disease is Alzheimer's Disease or Lewy Body Dementia.

In a third aspect of the invention, a method is presented for treating or preventing the neurotoxicity associated with exposure to a nerve agent by identifying a patient suffering from or at risk of exposure to a nerve agent and administering to the patient a therapeutically-effective amount of a compound represented by the following formula:

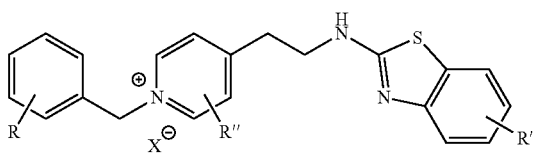

or a salt, ester or prodrug thereof, wherein the phenyl ring may contain one or more R substituent groups, the benzothiazole ring may contain one or more R' substituent groups, and the pyridine ring may contain one or more R" substituent groups; and wherein R is selected from the group consisting of hydrogen, a halogen, alkyl, cycloalkyl, aryl, heteroaryl, a 3' hydroxyl, a 5' hydroxyl, acyl, alkoxy, 6 arboxyesters, carboxythiol ester, and an amide, any carbon atom of which may be optionally substituted;

R' is selected from the group consisting of hydrogen, a halogen, alkyl, cycloalkyl, aryl, heteroaryl, a 3' hydroxyl, a 5' hydroxyl, acyl, alkoxy, 6 arboxyesters, carboxythiol ester, and an amide, any carbon atom of which may be optionally substituted;

R" is selected from the group consisting of hydrogen, a halogen, alkyl, cycloalkyl, aryl, heteroaryl, a 3' hydroxyl, a 5' hydroxyl, acyl, alkoxy, carboxy ester, carboxythiol ester, and an amide, any carbon atom of which may be optionally substituted; and X is selected from the group consisting of an organic or inorganic negatively-charged ion.

In one embodiment, the patient is a human. In another embodiment, the patient is a domesticated animal. In a further embodiment, the nerve agent is an organophosphate agent, such as tabun, sarin, soman, cyclosarin, GV, EA-3148, VE, VG, VM, VR, VX, a Novichok agent, dichlorvos, malathion, parathion, azinphos methyl, or chlorpyrifos.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

As used herein, the singular form "a," "an," and "the" include plural references unless the context clearly dictates otherwise. For example, the term "a cell" includes a plurality of cells, including mixtures thereof. The term "a nucleic acid molecule" includes a plurality of nucleic acid molecules.

The term "acyl" as used herein, alone or in combination, refers to a carbonyl attached to an alkenyl, alkyl, aryl, cycloalkyl, heteroaryl, heterocyclyl, or any other moiety where the atom attached to the carbonyl is carbon. An "acetyl" group refers to a —C(O)CH$_3$ group.

An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl" as used herein, alone or in combination, refers to a straight-chain or branched-chain hydrocarbon radical having one or more double bonds optionally substituted and containing from 2 to 20, preferably 2 to 6, carbon atoms. Alkenyl refers to a carbon-carbon double bond system attached at two or more positions such as ethenylene [(—CH=CH—),(—C::C—)]. Examples of alkenyl radicals include ethenyl, propenyl, 2-methylpropenyl, 1,4-butadienyl and the like.

The term "alkoxy" as used herein, alone or in combination, refers to an alkyl ether radical, optionally substituted wherein the term alkyl is as defined below. Examples of alkyl ether radicals include methoxy, ethoxy, n-propoxy, isopropoxy, n-butoxy, iso-butoxy, sec-butoxy, tert-butoxy, and the like.

The term "alkyl" as used herein, alone or in combination, refers to a straight-chain or branched-chain alkyl radical optionally substituted containing from 1 to 20 and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like.

The term "alkylamino" as used herein, alone or in combination, refers to an alkyl group optionally substituted attached to the parent molecular moiety through au amino group. Alkylamino groups may be mono- or dialkylated, forming groups such as, for example, N-methylamino, N-ethylamino, N,N-dimethylamino, N,N-ethylmethylamino and the like.

The term "alkylthio" as used herein, alone or in combination, refers to an alkyl thioether (R—S—) radical wherein the term alkyl is as defined above and wherein the sulfur may be singly or doubly oxidized. Examples of alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl" as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynyl" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like.

The term "amido" as used herein, alone or in combination, refer to an amino group as described below attached to the parent molecular moiety through a carbonyl group, or vice versa.

The term "amino" as used herein, alone or in combination, refers to —NRR', wherein R and R' are independently selected from the group consisting of hydrogen, alkyl acyl, heteroalkyl, aryl, cycloalkyl, heteroaryl, and heterocycloalkyl, any of which may themselves be optionally substituted.

The term "aryl" as used herein, alone or in combination, means a carbocyclic aromatic system containing one, two or three rings wherein such rings may be attached together in a pendent manner or may be fused optionally substituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 12 carbon atoms.

The terms "arylalkyl" or "aryalkyl" as used herein, alone or in combination, refers to an aryl group attached to the parent molecular moiety through an alkyl group.

The term "aryloxy" as used herein, alone or in combination, refers to an aryl group attached to the parent molecular moiety through an oxygen atom.

The term "polyether radical" means a polyether radical containing from 2 to 6 carbon atoms interrupted with at least one oxygen atom, such as methoxymethyl, ethoxymethyl or methoxyethoxymethyl radicals or methoxyethyl.

The terms "benzo" and "benz" as used herein, alone or in combination, refer to the divalent radical C$_6$H$_4$=derived from benzene. Examples include benzothiophene and benzimidazole.

The terms "carbamate" and "carbamoyl" as used herein, alone or in combination, refers to an ester of carbamic acid (—NHCOO—) which may be attached to the parent molecular moiety from either the nitrogen or acid end, and which may be optionally substituted as defined herein.

The term "carbonyl" as used herein, when alone includes formyl [—C(O)H] and in combination is a —C(O)— group.

The term "carboxy" as used herein, refers to —(C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano" as used herein, alone or in combination, refers to —CN.

The term "cycloalkyl" or, alternatively, "carbocycle", as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo-fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester" as used herein, alone or in combination, refers to a carboxy group bridging two moieties linked at carbon atoms.

The term "ether" as used herein, alone or in combination, refers to an oxygen atom bridging two moieties linked at carbon atoms.

The terms "halo" or "halogen" as used herein, alone or in combination, refers to fluorine, chlorine, bromine, or iodine.

The term "haloalkyl" as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CHF—), difluoromethylene (—CF$_2$—), chloromethylene (—CHCl—) and the like.

The term "heteroalkyl" as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl" as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, phenanthrolinyl, dibenzofuranyl, acridinyl, phenanthridinyl, xanthenyl and the like.

The terms "heterocycloalkyl" and, interchangeably, "heterocyclyl", as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocyclyl" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocyclyl groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocyclyl groups may be optionally substituted unless specifically prohibited.

The term "hydroxyl" as used herein, alone or in combination, refers to —OH.

The phrase "in the main chain" refers to the longest contiguous or adjacent chain of carbon atoms starting at the point of attachment of a group to the compounds of this invention.

The phrase "linear chain of atoms" refers to the longest straight chain of atoms independently selected from carbon, nitrogen, oxygen and sulfur.

The term "lower" as used herein, alone or in combination, means containing from 1 to and including 6 carbon atoms.

The term "negatively-charged ion" as used herein, refers to any negatively-charged ion or molecule, either inorganic (e.g., Cl$^-$, Br$^-$, or I$^-$) organic (e.g., TsO— (i.e., tosylate)).

The term "nitro" as used herein, alone or in combination, refers to —NO$_2$.

The term "perhaloalkyl" as used herein, alone or in combination, refers to an alkyl group where all of the hydrogen atoms are replaced by halogen atoms.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstitutedsilyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Optical isomers are compounds with the same molecular formula but differ in the way they rotate plane polarized light. There are two types of optical isomers. The first type of optical isomers are compounds that are mirror images of one another but cannot be superimposed on each other. These isomers are called "enantiomers." The second type of optical isomers are molecules that are not mirror images but each molecule rotates plane polarized light and are considered optically-active. Such molecules are called "diastereoisomers." Diastereoisomers differ not only in the way they rotate plane polarized light, but also their physical properties. The term "optical isomer" comprises more particularly the enantiomers and the diastereoisomers, in pure form or in the form of a mixture.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "imaging agent" as used herein refers to any moiety useful for the detection, tracing, or visualization of a compound of the invention when coupled thereto. Imaging agents include, e.g., an enzyme, a fluorescent label (e.g., fluorescein), a luminescent label, a bioluminescent label, a magnetic label, a metallic particle (e.g., a gold particle), a nanoparticle, an antibody or fragment thereof (e.g., a Fab, Fab', or F(ab')$_2$ molecule), and biotin. An imaging agent can be coupled to a compound of the invention by, for example, a covalent bond, ionic bond, van der Waals interaction or a hydrophobic bond. An imaging agent of the invention can be a radiolabel coupled to a compound of the invention, or a radioisotope incorporated into the chemical structure of a compound of the invention. Methods of detecting such imaging agents are well known to those having skill in the art.

The term "nerve agent" as used herein, refers to any toxic chemical that disrupts the function of neurons, specifically the transduction of action potentials. Nerve agents have historically been weaponized or used as insecticides. Common nerve agents are organophosphates, including but not limited to, diisopropylfluorophosphate (DFP), GA (tabun), GB (sarin), GD (soman), CF (cyclosarin), GE, CV, YE, VG (amiton), VM, VR(RVX or Russian VX), VS, and VX. Other chemical warfare agents of interest are phosphonothioic acid, methyl-, S-(2-bis(1-methylethylamino)-ethyl) O-ethyl ester O-ethyl; S-(2-diisopropylaminoethyl)methylphosphonothiolate; S-2-Diisopropylaminoethyl O-ethyl methylphosphonothioate; S-2((2-Diisopropylamino)ethyl) O-ethyl methylphosphonothiolate; O-ethyl S-(2-diisopropylaminoethyl) methylphosphonothioate; O-ethyl S-(2-diisopropylaminoethyl)methylthiolphosphonoate; S-(2-diisopropylaminoethyl) o-ethyl methyl phosphonothiolate; Ethyl-5-dimethylaminoethyl methylphosphonothiolate VX EA 1701; and TX60.

The term "neurodegenerative disorder" as used herein, refers to any disease, disorder, condition, or symptom characterized by the structural or functional loss of neurons. Neurodegenerative disorders include, e.g., Alzheimer's Disease, Parkinson's Disease, Huntington's Disease, Lewy Body Dementia, and amyotrophic lateral sclerosis.

The phrase "therapeutically effective" is intended to qualify the amount of active ingredients used in the treatment of a disease or disorder. This amount will achieve the goal of reducing or eliminating the disease or disorder.

The term "therapeutically acceptable" refers to those compounds (or salts, esters, prodrugs, tautomers, zwitterionic forms, etc. thereof) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, rabbits, and rodents (e.g., rats, mice, and guinea pigs).

The term "prodrug" refers to a compound that is made more active in vivo. Certain compounds of the present invention may also exist as prodrugs, as described in *Hydrolysis in Drug and Prodrug Metabolism: Chemistry, Biochemistry, and Enzymology*, Testa, Bernard and Wiley-VHCA, Zurich, Switzerland 2003. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bio-available by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug is a compound that is administered as an ester (the "prodrug"), but then is metabolically hydrolyzed to the carboxylic acid, the active entity. Additional examples include peptidyl derivatives of a compound.

The compounds of the invention can exist as therapeutically acceptable salts. The present invention includes compounds listed above in the form of salts, in particular acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Stahl, P. Heinrich, *Pharmaceutical Salts: Properties, Selection, and Use*, Wiley-VCHA, Zurich, Switzerland (2002).

The term "therapeutically acceptable salt" as used herein, represents salts or zwitterionic forms of the compounds of the present invention which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

DETAILED DESCRIPTION OF THE INVENTION

Figure 1:
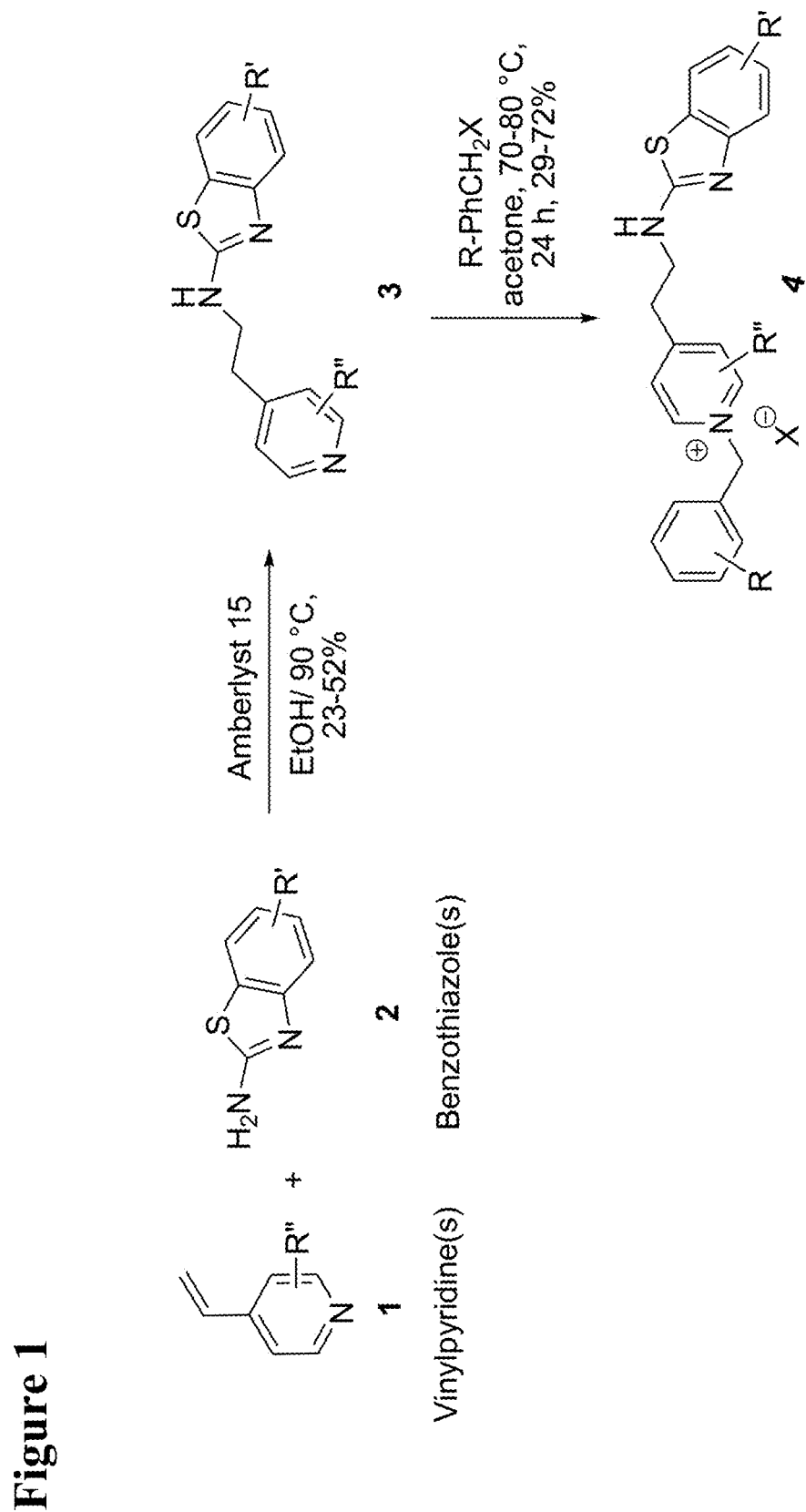
FIG. 1 is a diagram illustrating the chemical synthesis of the benzothiazole-based pyridinium compounds of the invention.
Figure 2:
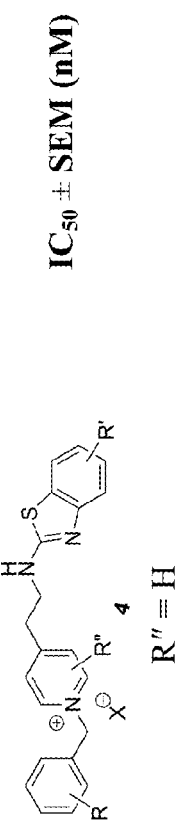
FIG. 2 is a table showing the inhibitory activity ($IC_{50}$) and selectivity of five compounds of the invention. $IC_{50}$ is defined as the concentration of compounds that reduces enzyme activity by 50% with respect to control experiment (without inhibitors) and is determined from the plot of % AChE activity vs. Log (concentration). All values are expressed as mean±standard error of the mean of at least three experiments. Selectivity for AChE with respect to BChE (higher value indicates greater selectivity for AChE with respect to BChE).

The present invention involves novel benzothiazole-based pyridinium compounds that bind and inhibit cholinesterase enzymes, such as acetylcholinesterase ("AChE") and pseudocholinesterase ("BChE"). The inhibitory properties of the compounds of the invention can therefore be used to treat or prevent diseases, disorders, conditions, or symptoms in a patient (e.g., a human) that involve, directly or indirectly, acetycholine or butyrylcholine metabolism, either caused naturally (e.g., by a neurodegenerative disease, such as Alzheimer's disease) or by exposure to an artificial agent (e.g., a nerve agents or insecticides).

A class of benzothiazole-based pyridinium compounds is presented and defined by structural Formula I:

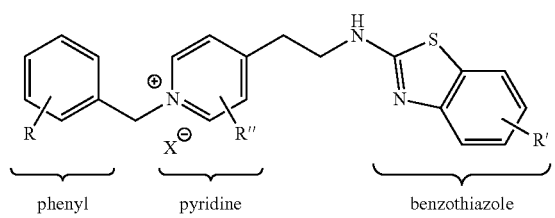

phenyl    pyridine    benzothiazole or a salt, ester or prodrug thereof, wherein the phenyl ring may contain one or more R substituent groups, the benzothiazole ring may contain one or more R' substituent groups, and the pyridine ring may contain one or more R" substituent groups; and wherein R is selected from the group consisting of hydrogen, a halogen, alkyl, cycloalkyl, aryl, heteroaryl, a 3' hydroxyl, a 5' hydroxyl, acyl, alkoxy, carboxyester, carboxythiolester, and an amide, any carbon atom of which may be optionally substituted;

R' is selected from the group consisting of hydrogen, a halogen, alkyl, cycloalkyl, aryl, heteroaryl, a 3' hydroxyl, a 5' hydroxyl, acyl, alkoxy, carboxyester, carboxythiolester, and an amide, any carbon atom of which may be optionally substituted;

R" is selected from the group consisting of hydrogen, a halogen, alkyl, cycloalkyl, aryl, heteroaryl, a 3' hydroxyl, a 5' hydroxyl, acyl, alkoxy, carboxyester, carboxythiolester, and an amide, any carbon atom of which may be optionally substituted; and X is selected from the group consisting of an organic or inorganic negatively-charged ion.

Compounds of the invention derived from Formula I include, but are not limited to, the following chemical structures:

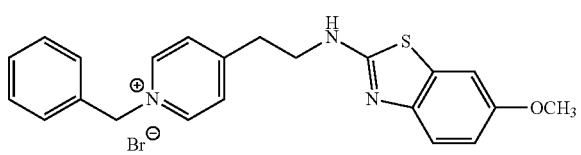 [SMILES: COc1ccc2nc(NCCc3cc[n+](Cc4ccccc4)cc3)sc2c1 ; [Br-]]

1-Benzyl-4-[2-(6-methoxy-benzothiazol-2-yl)-aminoethyl]-pyridinium bromide 4a

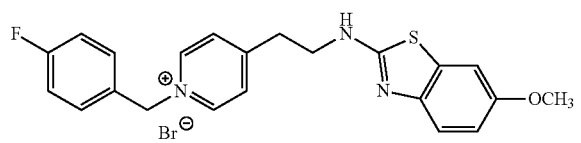 [SMILES: COc1ccc2nc(NCCc3cc[n+](Cc4ccc(F)cc4)cc3)sc2c1 ; [Br-]]

1-(4-Fluoro-benzyl)-4-[2-(6-methoxy-benzothiazol-2-yl)-aminoethyl]-pyridinium bromide 4b

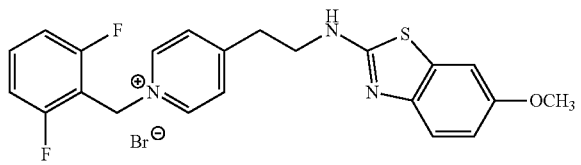 [SMILES: COc1ccc2nc(NCCc3cc[n+](Cc4c(F)cccc4F)cc3)sc2c1 ; [Br-]]

1-(2,6-Difluoro-benzyl)-4-[2-(6-methoxy-benzothiazol-2-yl)-aminoethyl]-pyridinium bromide 4c

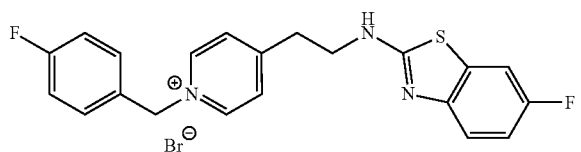 [SMILES: Fc1ccc(C[n+]2ccc(CCNc3nc4ccc(F)cc4s3)cc2)cc1 ; [Br-]]

1-(4-Fluoro-benzyl)-4-[2-(6-fluoro-benzothiazol-2-yl)-aminoethyl]-pyridinium bromide 4d

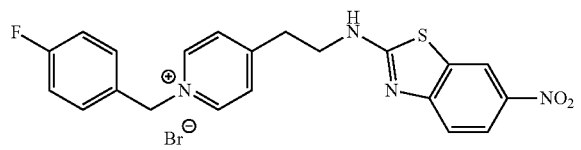 [SMILES: O=[N+]([O-])c1ccc2nc(NCCc3cc[n+](Cc4ccc(F)cc4)cc3)sc2c1 ; [Br-]]

1-(4-Fluoro-benzyl)-4-[2-(6-nitro-benzothiazol-2-yl)-aminoethyl]-pyridinium bromide 4e Neurodegenerative Disorders One or more compounds of the invention can be used to treat a patient (e.g., a human) at risk of developing or already suffering from a neurodegenerative disorder, such as Alzheimer's Disease ("AD") or Lewy Body Dementia, in which inhibition of a cholinesterase (e.g., AChE) delays, stops, or reverses disease progression or partially or completely alleviates the symptoms (e.g., memory loss) of the neurodegenerative disease.

Nerve Agents

One or more compounds of the invention can also be used to prevent or treat exposure of a patient (e.g., a human) to a nerve agent, such as an organophosphate-based chemical weapon or insecticide. Such treatment or prophylaxis serves to competitively bind cholinesterase (e.g., AChE) molecules in a patient (e.g., a human) against organophosphate nerve agents. The preferential binding of cholinesterase molecules (e.g., AChE) by the compounds of the invention can prevent, reduce, or treat the symptoms or conditions typically suffered by a patient (e.g., a human) upon exposure to organophosphate nerve agents.

The compounds of the invention can be particularly useful for the prophylactic treatment of members of armed forces at risk of exposure to nerve agents, especially weaponized nerve agents, in the course of duty. Similarly, the compounds of the invention can be used to treat or prophylax a patient (e.g., a human) that may be exposed to organophosphate nerve agents, such as insecticides, during the course of employment (e.g., agricultural workers or livestock).

Methods of Prevention and Treatment

The compounds of the invention can be used to treat a patient (e.g., a human) that suffers from or is at risk of suffering from a disease, disorder, condition or symptom described herein. The compounds of the invention can be used alone or in combination with other agents and compounds in methods of treating or preventing, e.g., a neurodegenerative disease (e.g., Alzheimer's Disease) or exposure to a nerve agent. Each such treatment described above includes the step of administering to a patient in need thereof a therapeutically effective amount of the compound of the invention described herein to delay, reduce or prevent such disease, disorder, condition, or symptom.

Besides being useful for human treatment, the compounds and formulations of the present invention are also useful for the treatment of animals, e.g., the veterinary treatment of domesticated animal, companion animals (e.g., dogs and cats), exotic animals, farm animals (e.g., ungulates, including horses, cows, sheep, goats, and pigs), and animals used in scientific research (e.g., rodents).

The compounds of the invention presented herein may be also useful in enhancing learning, cognition and/or memory, regulating cell growth, providing neuroprotection and the like. The compounds presented herein may also be used for treating dermatological complaints associated with a keratinization disorder relating to cell differentiation and proliferation, especially for treating acne, for treating other dermatological complaints, with or without cell proliferation disorder, and especially all forms of psoriasis, for treating all dermal or epidermal proliferations, for preventing or treating cicatrization disorders, in the treatment of dermatological or general complaints with an immunological component, in the treatment of skin disorders caused by exposure to UV radiation, and also for combating sebaceous function disorders, for repairing or combating aging of the skin, for preventing or treating cicatrization disorders, or in the treatment of pigmentation disorders.

Compound Administration and Formulation

Basic addition salts can be prepared during the final isolation and purification of the compounds by reaction of a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N- dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid. The novel compounds described herein can be prepared in a form of pharmaceutically acceptable salts that will be prepared from nontoxic inorganic or organic bases including but not limited to aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally-occurring substituted amines, cyclic amines, and basic ion exchange resins, such as arginine, betaine, caffeine, choline, ethylamine, 2-diethylaminoethano, 1,2-dimethylaminoethanol, ethanolamine, ethylenediamine, N-ethyl-morpholine, N-ethylpiperidine, glucamine, glucosamine, histidine, hydroxylamine, isopropylamine, lysine, methylglucamine, morpholine, piperazine, piperidine, polyamine resins, procaine, purines, theobromine, triethylamine, trimethylamine, trishydroxylmethyl amino methane, tripropyl amine, and tromethamine.

If the compounds of the invention are basic, salts could be prepared in a form of pharmaceutically acceptable salts that will be prepared from nontoxic inorganic or organic acids including but not limited to hydrochloric, hydrobromic, phosphoric, sulfuric, tartaric, citric, acetic, fumaric, alkylsulphonic, naphthalenesulphonic, para-toluenesulphonic, camphoric acids, benzenesulfonic, benzoic, camphorsulfonic, citric, ethanesulfonic, gluconic, glutamic, isethonic, lactic, maleic, malic, mandelic, methanesulfonic, mucic, nitric, pamoic, pantothenic, phosphoric, and succinic.

While it may be possible for the compounds of the invention to be administered as the raw chemical, it is also possible to present them as a pharmaceutical formulation. Accordingly, the present invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the present invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds of the invention may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds of the invention may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compounds of the invention may take the form of tablets, lozenges, pastilles, or gels formulated in conventional manner. Such compositions may comprise the active ingredient in a flavored basis such as sucrose and acacia or tragacanth.

The compounds of the invention may also be formulated in rectal compositions such as suppositories or retention enemas, e.g., containing conventional suppository bases such as cocoa butter, polyethylene glycol, or other glycerides.

Compounds of the invention may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include solid, liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Via the topical route, the pharmaceutical composition according to the invention may be in the form of liquid or semi liquid such as ointments, or in the form of solid such as powders. It may also be in the form of suspensions such as polymeric microspheres, or polymer patches and hydrogels allowing a controlled release. This topical composition may be in anhydrous form, in aqueous form or in the form of an emulsion. The compounds are used topically at a concentration generally of between 0.001% and 10% by weight and preferably between 0.01% and 1% by weight, relative to the total weight of the composition.

For administration by inhalation, the compounds according to the invention are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.1 to 500 mg/kg per day. The dose range for adult humans is generally from 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

Compounds according to the invention can be administered at a daily dose of about 0.001 mg/kg to 100 mg/kg of body weight, in 1 to 3 dosage intakes. Further, compounds can be used systemically, at a concentration generally of between 0.001% and 10% by weight and preferably between 0.01% and 1% by weight, relative to the weight of the composition.

The amount of active ingredient that may be combined with the carrier materials to produce a single dosage form will vary depending upon the host treated and the particular mode of administration.

The compounds of the invention can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds of the invention described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for pain involving administration of one of the compounds described herein, increased therapeutic benefit may result by also providing the patient with another therapeutic agent for pain. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of the compounds of the invention together with inert or active compounds, or other drugs including wetting agents, flavor enhancers, preserving agents, stabilizers, humidity regulators, pH regulators, osmotic pressure modifiers, emulsifiers, UV-A and UV-B screening agents, antioxidants, depigmenting agents such as hydroquinone or kojic acid, emollients, moisturizers, for instance glycerol, PEG 400, or urea, antiseborrhoeic or antiacne agents, such as S-carboxymethylcysteine, S-benzylcysteamine, salts thereof or derivatives thereof, or benzoyl peroxide, antibiotics, for instance erythromycin and tetracyclines, chemotherapeutic agent, for example, paclitaxel, antifungal agents such as ketoconazole, agents for promoting regrowth of the hair, for example, minoxidil (2,4-diamino-6-piperidinopyrimidine 3-oxide), non-steroidal anti-inflammatory agents, carotenoids, and especially p-carotene, antipsoriatic agents such as anthralin and its derivatives, eicosa-5,8,11,14-tetraynoic acid and eicosa-5,8,11-triynoic acid, and esters and amides thereof, retinoids, e.g., RAR or RXR receptor ligands, which may be natural or synthetic, corticosteroids or oestrogens, alpha-hydroxy acids and a-keto acids or derivatives thereof, such as lactic acid, malic acid, citric acid, and also the salts, amides or esters thereof, or p-hydroxy acids or derivatives thereof, such as salicylic acid and the salts, amides or esters thereof, ion-channel blockers such as potassium-channel blockers, or alternatively, more particularly for the pharmaceutical compositions, in combination with medicaments known to interfere with the immune system, anticonvulsant agents include, and are not limited to, topiramate, analogs of topiramate, carbamazepine, valproic acid, lamotrigine, gabapentin, phenytoin and the like and mixtures or pharmaceutically acceptable salts thereof. A person skilled in the art will take care to select the other compound(s) to be added to these compositions such that the advantageous properties intrinsically associated with the compounds of the invention are not, or are not substantially, adversely affected by the envisaged addition.

In any case, the multiple therapeutic agents (at least one of which is a compound of the present invention) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, methods for treating diseases, disorders, conditions, or symptoms in a patient (e.g., a human or animal) in need of such treatment are presented herein, the methods comprising the step of administering to the patient an amount of a compound of the invention effective to reduce or prevent the disease, disorder, condition, or symptom, in combination with at least one additional agent for the treatment of said disorder that is known in the art.

In a related aspect, therapeutic compositions having at least one novel compound of the invention described herein can be administered in combination with one or more additional agents for the treatment of any of the diseases, disorders, conditions, or symptoms described herein.

It is understood that the foregoing examples are merely illustrative of the present invention. Certain modifications of the articles and/or methods employed may be made and still achieve the objectives of the invention. Such modifications are contemplated as within the scope of the claimed invention.

EXAMPLES

Example 1

Synthesis of Compositions of the Invention

The present invention relates to the discovery of benzothiazole-based pyridinium compounds with dual-site binding ability. A general synthetic strategy for compounds proposed in present invention is depicted in FIG. 1. The starting materials (4-vinylpyridines 1 and benzothiazoles 2) are relatively inexpensive or easily accessible, and reagents and conditions are mild.

The method of synthesis for compounds of the invention is as follows: To a mixture of 4-vinylpyridine (1, 2.5 mmol) and substituted 2-amino-benzothiazoles (2, 2.5 mmol) in ethanol (3 mL) was added Amberlyst-15 (20% w/w with respect to vinylpyridine). The reaction mixture was refluxed at 90-100° C. for 24 h. The reaction was cooled to room temperature and the catalyst was filtered off Solvent evaporation and further purification by silica gel column chromatography using hexane/ethyl acetate solvent system yielded 4-(benzothiazol-2-yl)-aminoethyl pyridines 3. These substituted aminoethylpyridines (3, 1 mmol) and the alkylating agent (1.5 mmol) in acetone (20 mL) were stirred at 60-80° C. for 4-5 h. The mixture was cooled to room temperature, the precipitate collected, washed with acetone (3×20 mL), dried under vacuum to get desired compounds 4a-4e. All compounds were characterized by $^1$H NMR, $^{13}$C NMR, ESI-MS and HRMS.

Example 2

Binding Affinity/Docking Studies

Docking studies were performed using the program AutoDockVina version 1.0.2 (http://vina.scripps.edu) software. Acetylcholinesterase structure (AChE-E2020 complex) was obtained from the RCSB Protein Data Bank (http://www.rcsb.org); the PDB ID was 1EVE. Ligand structures were drawn using ChemDraw Ultra; energy was minimized using MM2 and MOPAC jobs in Chem3D ultra and saved in .pdb format. AutoDockTools (ADT) version 1.5.4 (http://mgltools.scripps.edu) was used for protein and ligand preparation. Since the positions of most of the water molecules in the crystal structure of AChE-E2020 are unlikely to be conserved, water molecules were removed before docking Hydrogen atoms were added to all amino acids. Kollman charges for all atoms in AChE were assigned by using AutoDock Tools. The search and scoring grid for Autodock was centered in the cavity. The docking site for the ligands on 1EVE was defined by establishing a cube at the geometrical center of the native ligand E2020 (Donepezil). The torsional bonds of ligands were set free by Ligand module in ADT. The structures were then saved in PDBQT file format, for input into AutoDockVina. All computations were carried out on a MacBook.Ligands are ranked based on an energy scoring function and, to speed up the score calculation, a grid-based protein-ligand interaction is used. The docking results from each calculation were clustered on the basis of root-mean square deviation (RMSD) between the Cartesian coordinates of the ligand atoms and were ranked according to the binding free energy.

Figure 3A:
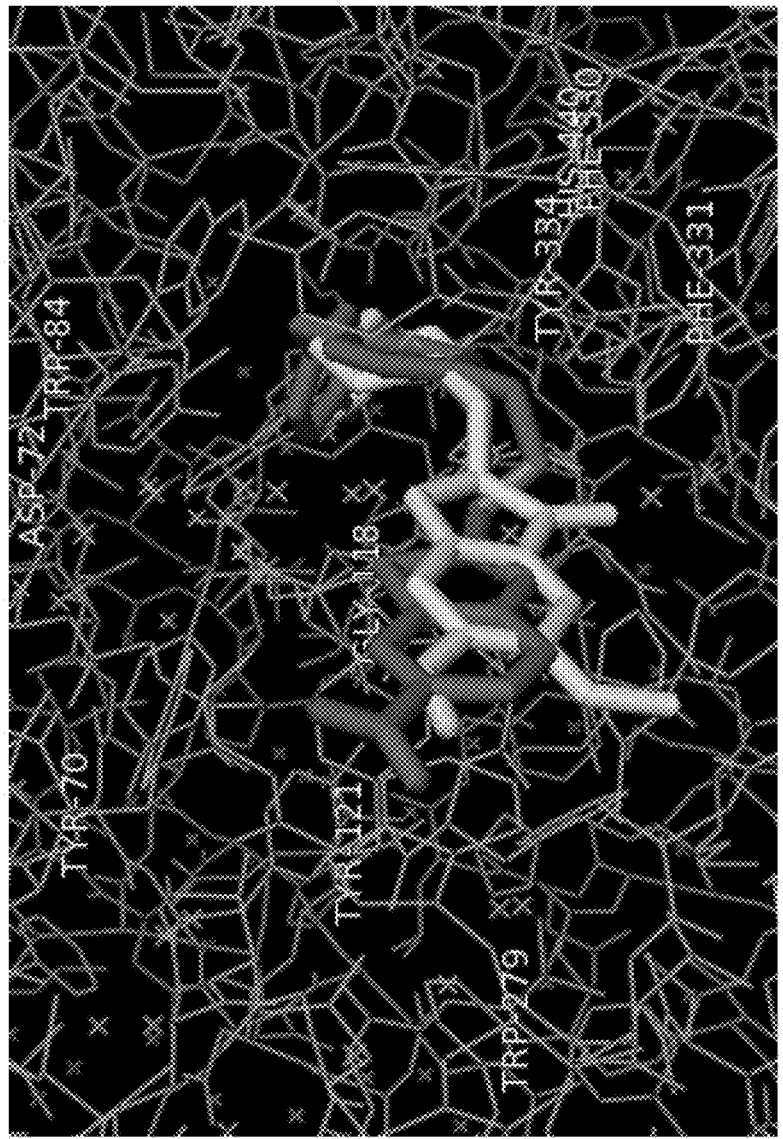
FIG. 3 are computer software-generated receptor-ligand binding images that show a comparison between donepezil (yellow) and 1-(4-fluoro-benzyl)-4-[2-(6-nitro-benzothiazol-2-yl)-aminoethyl]-pyridinium bromide 4e (red) in the AChE gorge. (a) top view; (b) side view of the gorge.
Figure 3B:
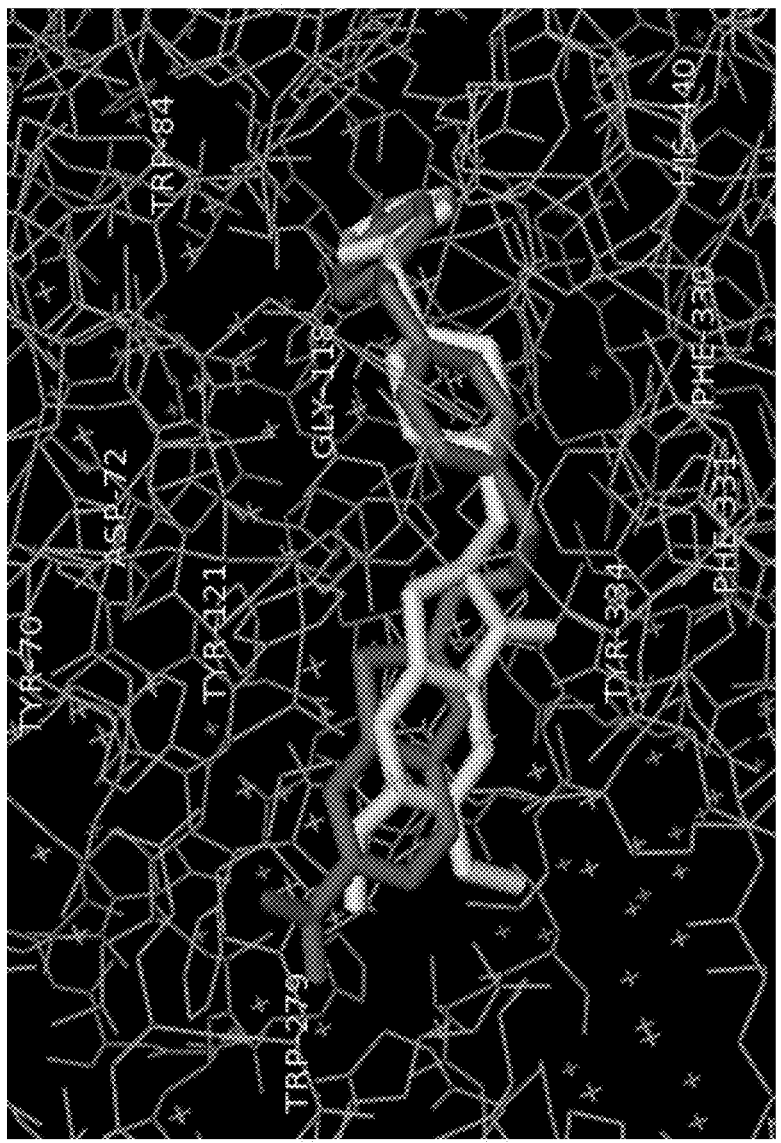

Docking studies revealed the conformation and orientation of the ligand 1-(4-fluoro-benzyl)-4-[2-(6-nitro-benzothiazol-2-yl)-aminoethyl]-pyridinium bromide 4e in the AChE binding site. Like donepezil, ligand 1-(4-fluoro-benzyl)-4-[2-(6-nitro-benzothiazol-2-yl)-aminoethyl]-pyridinium bromide 4e also spans the entire aromatic gorge of AChE. It interacts with peripheral anionic site residues Tyr70 and Trp279 as well as with the ammonium binding site residues Trp84, Phe330 and Asp72, and phenyl group binding residues Trp84 and Phe330 (FIG. 3).

All Embodiments

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Other embodiments are within the claims.

What is claimed is:

1. A compound represented by the formula:

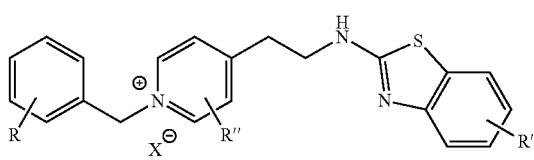

or a salt or ester thereof, wherein the phenyl ring may contain one or more R substituent groups, the benzothiazole ring may contain one or more R' substituent groups, and the pyridine ring may contain one or more R" substituent groups; and wherein R is selected from the group consisting of hydrogen, a halogen, alkyl, cycloalkyl, aryl, heteroaryl, a 3' hydroxyl, a 5' hydroxyl, acyl, alkoxy, carboxyester, carboxythiolester, and an amide, any carbon atom of which may be optionally substituted;

R' is selected from the group consisting of hydrogen, a halogen, alkyl, cycloalkyl, aryl, heteroaryl, a 3' hydroxyl, a 5' hydroxyl, acyl, alkoxy, carboxyester, carboxythiolester, and an amide, any carbon atom of which may be optionally substituted;

R" is selected from the group consisting of hydrogen, a halogen, alkyl, cycloalkyl, aryl, heteroaryl, a 3' hydroxyl, a 5' hydroxyl, acyl, alkoxy, carboxyester, carboxythiolester, and an amide, any carbon atom of which may be optionally substituted; and X is selected from the group consisting of an organic or inorganic negatively-charged ion.

2. The compound of claim 1, wherein said compound is selected from the group consisting of the following formulae:

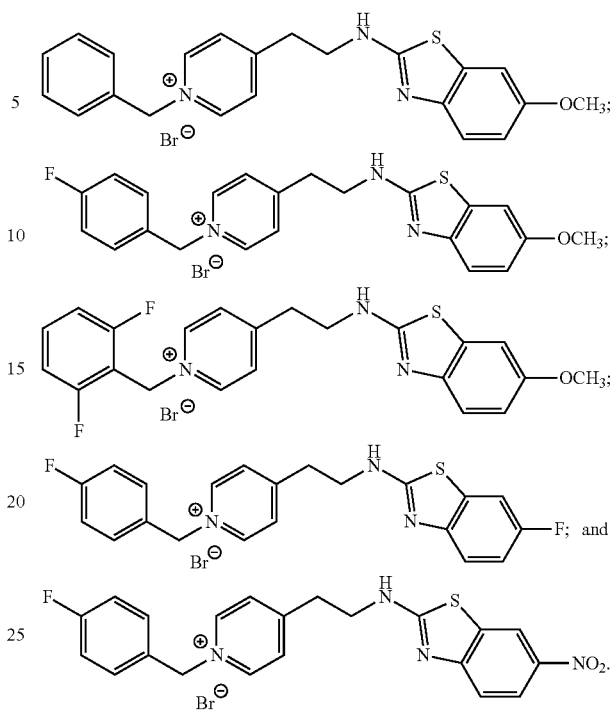

3. The compound of claim 1, further comprising a pharmaceutically acceptable excipient.

4. A method for treating or preventing the development of a neurodegenerative disease comprising the steps of
identifying a patient suffering from or at risk of developing a neurodegenerative disease; and
administering to said patient a therapeutically-effective amount of a compound represented by the formula:

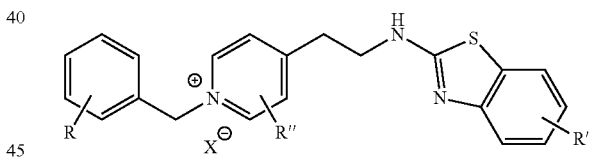

or a salt or ester thereof, wherein the phenyl ring may contain one or more R substituent groups, the benzothiazole ring may contain one or more R' substituent groups, and the pyridine ring may contain one or more R" substituent groups; and wherein R is selected from the group consisting of hydrogen, a halogen, alkyl, cycloalkyl, aryl, heteroaryl, a 3' hydroxyl, a 5' hydroxyl, acyl, alkoxy, carboxyester, carboxythiolester, and an amide, any carbon atom of which may be optionally substituted;

R' is selected from the group consisting of hydrogen, a halogen, alkyl, cycloalkyl, aryl, heteroaryl, a 3' hydroxyl, a 5' hydroxyl, acyl, alkoxy, carboxyester, carboxythiolester, and an amide, any carbon atom of which may be optionally substituted;

R" is selected from the group consisting of hydrogen, a halogen, alkyl, cycloalkyl, aryl, heteroaryl, a 3' hydroxyl, a 5' hydroxyl, acyl, alkoxy, carboxyester, carboxythiolester, and an amide, any carbon atom of which may be optionally substituted; and X is selected from the group consisting of an organic or inorganic negatively-charged ion.

5. The method of claim 4, wherein said patient is a human.

6. The method of claim 4, wherein said neurodegenerative disease is Alzheimer's Disease or Lewy Body Dementia.

7. A method for treating exposure to a nerve agent comprising the steps of
identifying a patient suffering from exposure to a nerve agent; and
administering to said patient a therapeutically-effective amount of a compound represented by the formula:

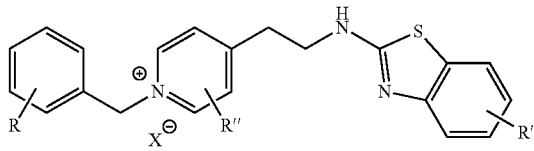

or a salt or ester thereof, wherein the phenyl ring may contain one or more R substituent groups, the benzothiazole ring may contain one or more R' substituent groups, and the pyridine ring may contain one or more R" substituent groups; and wherein
R is selected from the group consisting of hydrogen, a halogen, alkyl, cycloalkyl, aryl, heteroaryl, a 3' hydroxyl, a 5' hydroxyl, acyl, alkoxy, carboxyester, carboxythiolester, and an amide, any carbon atom of which may be optionally substituted;

R' is selected from the group consisting of hydrogen, a halogen, alkyl, cycloalkyl, aryl, heteroaryl, a 3' hydroxyl, a 5' hydroxyl, acyl, alkoxy, carboxyester, carboxythiolester, and an amide, any carbon atom of which may be optionally substituted;

R" is selected from the group consisting of hydrogen, a halogen, alkyl, cycloalkyl, aryl, heteroaryl, a 3' hydroxyl, a 5' hydroxyl, acyl, alkoxy, carboxyester, carboxythiolester, and an amide, any carbon atom of which may be optionally substituted; and X is selected from the group consisting of an organic or inorganic negatively-charged ion.

8. The method of claim 7, wherein said patient is a human.

9. The method of claim 7, wherein said patient is a domesticated animal.

10. The method of claim 7, wherein said nerve agent comprises an organophosphate agent.

11. The method of claim 10, wherein said organophosphate agent is selected from the group consisting of tabun, sarin, soman, cyclosarin, GV, EA-3148, VE, VG, VM, VR, VX, a Novichok agent, dichlorvos, malathion, parathion, azinphos methyl, and chlorpyrifos.

* * * * *